United States Patent [19] [11] Patent Number: 4,948,561
Hinckley et al. [45] Date of Patent: Aug. 14, 1990

[54] MULTIPLE LEVEL FILTER DEVICE AND KIT CONTAINING SAME

[75] Inventors: Charles C. Hinckley, Pittsford; Thomas J. Cummins, Rochester; Sheryl S. Sullivan, Hilton, all of N.Y.

[73] Assignee: Eastman Kodak Company, Rochester, N.Y.

[21] Appl. No.: 308,842

[22] Filed: Feb. 9, 1989

[51] Int. Cl.$^5$ ............................ G01N 33/53; B01D 63/08
[52] U.S. Cl. ................................. 422/61; 210/321.6; 210/321.64; 210/321.84; 210/490; 210/492; 210/506; 422/58; 422/101; 436/178; 436/808; 436/824; 436/825; 436/175
[58] Field of Search ............ 210/321.6, 321.64, 321.84, 210/323.1, 488, 489, 490, 491, 492, 500.27, 500.36, 506, 508, 509; 422/58, 59, 60, 61, 101; 436/178, 808, 824, 825, 175; 55/158

[56] References Cited

U.S. PATENT DOCUMENTS

| | | |
|---|---|---|
| 3,272,319 | 9/1966 | Brewer. |
| 3,873,682 | 3/1975 | Ogawa ............................ 210/505 |
| 4,087,363 | 5/1978 | Rosemeyer et al. ................. 210/489 |
| 4,210,418 | 7/1980 | Brown et al. ........................ 422/58 |
| 4,235,839 | 11/1980 | Vesterberg ............................ 422/58 |
| 4,318,986 | 3/1982 | Richardson et al. .................. 435/18 |
| 4,477,575 | 10/1984 | Vogel et al. ......................... 210/509 |
| 4,617,124 | 10/1986 | Pall et al. ............................ 210/508 |
| 4,624,929 | 11/1986 | Ullman ................................ 422/61 |
| 4,632,901 | 12/1986 | Valkirs et al. ......................... 422/58 |
| 4,707,450 | 11/1987 | Nason ................................. 422/61 |
| 4,770,853 | 9/1988 | Bernstein ............................. 422/58 |
| 4,786,474 | 11/1988 | Cooper ................................ 422/101 |
| 4,833,087 | 5/1989 | Hinckley ............................. 422/58 |
| 4,847,199 | 7/1989 | Snyder et al. ......................... 422/61 |
| 4,877,586 | 10/1989 | Devaney, Jr. et al. ................. 422/101 |

Primary Examiner—W. Gary Jones
Attorney, Agent, or Firm—Dana M. Schmidt

[57] ABSTRACT

A filter providing at least two different filtering pore sizes for coarse and fine filtering, and a kit containing such filter along with an immunoassay test device containing a membrane. The membrane is used to separate bound immunoassay labels from free labels. The coarse and fine filtering are provided preferably by two different, serially arranged filters, the filter with the fine pore size being selected with a pore size similar to that of the membrane of the assay device.

5 Claims, 2 Drawing Sheets

MULTIPLE LEVEL FILTER DEVICE AND KIT CONTAINING SAME

FIELD OF THE INVENTION

This invention relates to filters used to prepare a liquid containing extracted antigen, for assay using an immunoassay test device.

BACKGROUND OF THE INVENTION

Infectious diseases, such as that caused by Herpes Simplex Virus (HSV), are conventionally assayed by extracting body fluids, such as pus, from sores, and then extracting appropriate antigens from these fluids. Once the antigens are extracted, if present, they are passed through a filter to remove extraneous material, and then assayed in an immunoassay such as the device taught in commonly assigned U.S. Ser. No. 240,179 filed on Sept. 6, 1988, by Hinckley et al, which is a continuation-in-part application of U.S. Ser. No. 098,248 filed on Sept. 18, 1987, entitled "Sliding Valve for Vent of Liquid Collecting Compartment", now abandoned. Such a device has a membrane that captures the complexed antigen and antibodies used in the test, but allows unbound substances to pass through. This is sometimes called the bound/free separation step.

In certain tests, such as the HSV test, standard filtering has not been adequate to remove all the extraneous particulate matter. As a result, the extraneous particles end up on the membrane of the immunoassay device, clogging it and delaying the necessary flow-through of the free liquid and unbound substances such as labels.

Therefore, prior to this invention there has been a need to obtain antigens extracted from body fluids so as to render them more processable in a test device that uses a filter to separate bound substances from free substances.

SUMMARY OF THE INVENTION

We have constructed a multiple level filter device that is effective in solving the above-noted problems, by filtering out more of the materials that interfere with the immunoassay.

More specifically, in accord with one aspect of the invention, there is provided a multiple level filter device for a container used to process body fluids for an immunoassay using a binding membrane to trap detectible substances, the filter device comprising a holder having opposite ends for transmitting fluid flow through the device, and at least two filters between the ends, having different pore sizes, the one of the filters having the smaller pore size having a pore size substantially the same as that of the binding membrane.

In accord with another aspect of the invention there is provided a kit for extracting and testing an antigen from body fluids, the kit including an extraction tube to which a body fluid and an extracting reagent are added to produce a solution of extracted antigen, a filter tip for insertion into the tube after adding body fluids and the extracting agent, the tip being constructed to mate with the tube; a test device having filter means for passing the solution through and for attaching the extracted antigen, the filter means having a predetermined average pore size; and a container of labeled antibody for the antigen. The kit is improved in that the filter tip includes at least two filter media having two different predetermined pore sizes, one being a fine size and the other being a coarse size, the filter medium with the fine size being substantially the same pore size as the pore size of the test device filter means.

Accordingly, it is an advantageous feature of the invention that the presence of infectious diseases can be more readily assayed using antigen extracted from body fluids, by removal of material that otherwise clogs the filter used in the bound/free separation step.

Other advantageous features will become apparent upon reference to the following description of the preferred embodiments, when read in light of the attached drawings.

DESCRIPTION OF THE PREFERRED EMBODIMENTS

The invention is described hereinafter in connection with certain preferred embodiments wherein the assay is particularly suited for HSV, using the device of the aforesaid U.S. Ser. No. 240,179 and filter materials of preferred types. In addition, the invention is also useful regardless of the target antigen, using any immunoassay device, and any filter materials that will provide at least two filters with two different pore sizes, the smaller pore size being similar to that used in the immunoassay device. The plural filters can even be an integral one-piece filter with at least two serially positioned portions having different flow-intersecting pore sizes.

As is discussed hereinafter, the preferred immunoassay device 50, FIG. 3, through which the liquids must pass during the assay, uses a membrane filter 74, FIG. 4, sized to capture antigen-antibody complexes but not free labels. The purpose of this invention is to provide at least two levels of filters in the filtering step that precedes the actual assay—a coarse filtering step using a larger pore size to capture gross particles, and a fine filtering step that filters out the fine particles that otherwise can clog the membrane filter of the assay device 50. Accordingly, the invention provides that the fine filter have a pore size smaller than that of the coarse filter, namely one that is substantially the same as the pore size of the assay membrane filter 74. In preferred embodiments, the pore size of the assay membrane filter is in the range of from about 5 to about 10 microns. Accordingly, the fine filter size is from about 5 to about 10 microns in the multiple level filter.

Figure 2:
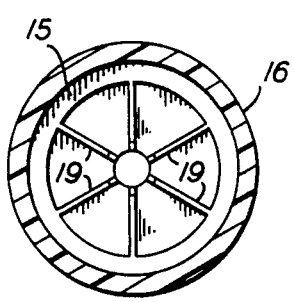
FIG. 2 is a section view taken generally along the line II—II of FIG. 1.
Figure 1:
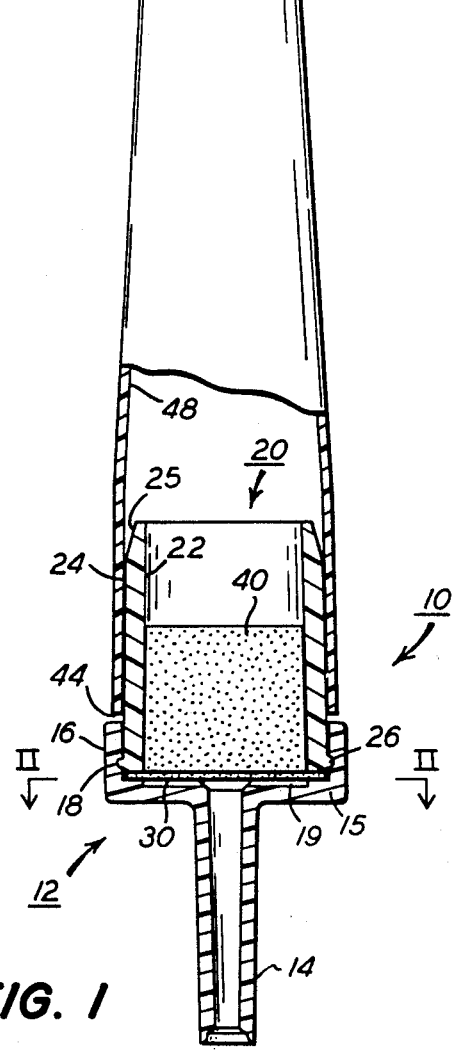
FIG. 1 is a section view of a filter device constructed in accordance with the invention.

As shown in FIG. 1, a preferred construction of the filter device 10 is one in which the body of the device is two snapped-together portions 12 and 20 that together provide opposite, open ends that transmit fluid flow through device 10. Portion 12 comprises a dispensing tip 14 attached to a base 15 having a lip 16. The interior of lip 16 is grooved at 18. Optionally, base 15 includes raised ribs 19, FIG. 2, to raise the membrane slightly above the surface of base 15, to provide faster flow away from the membrane to dispensing tip 14.

Portion 20 comprises a generally cylindrical tube having an inner surface 22 and an outer surface 24 that is preferably tapered at 25. Surface 24 is provided with a ridge 26 on the circumference, shaped to mate with groove 18 for the snap fit.

Sandwiched between the two portions 12 and 20 is the smaller pore-sized filter material, which is preferably a membrane 30 sized as noted above. That is, its pore sizes are similar to those of the membrane 74 of the assay device 50, discussed hereinafter. If the assay device membrane 74 is sized with 5 micron pore sizes, then the pore sizes of membrane 30 is from about 5 microns to about 10 microns, most preferably about 5 microns. If the membrane 74 of the assay device is sized with 10 micron pore sizes, then the pore size of membrane 30 is still about 5 to about 10 microns, but most preferably about 10 microns.

Filter sizes below 5 microns are not considered useful, either in the assay membrane 74 or in membrane 30. The reason is that below 5 microns, the antigen starts to be filtered out by filter membrane 30. In the assay device, sizes below 5 microns tend to decrease test sensitivity.

Filter sizes above 10 microns are considered less useful because, in the case of membrane 74 for device 50, more background color (or less sensitivity) occurs, making a clear determination of a positive reading more difficult.

Useful examples of a 5 micron-sized membrane include nylon membranes such as those manufactured under the tradename "LoProdyne" by Pall Corp., or HDC TM by Pall Corp. Useful examples of a 10 micron-sized membranes include nylon membranes such as those manufactured under the tradename "HDC" by Pall Corp. Either of these may be optionally precoated with a surfactant.

The coarsely-sized filter material is a plug 40 that is friction-fit within the interior surface 22 of cylindrical portion 20. The material preferably is selected with pore sizes effective to remove at least about 80% of all particles having a maximum dimension of from about 22 microns to about 25 microns. Useful examples of such material include plugs of polyester fibers or of molded porous polyethylene, such as a 25 micron polyethylene filter made by Porex. The polyester plugs are not readily characterized by a single pore size, such as the 5 or 10 micron pore sizes of membrane 30.

The filter device of the invention is preferably used with an extraction tube 42, having an open end 44 that is friction-fitted over surface 24 of the device, and a closed end 46. Sidewalls 48 of tube 42 are sufficiently flexible as to allow the sidewalls to be squeezed together, to pressurize the interior and force liquid therein to flow out through filters 40 and 30, and dispensing tip 14. As a result, tube 42 is used first without filter device 10 in place, so that patient body fluid from a sore or lesion is inserted along with extracting reagents, with open end 44 up. After extraction is complete, filter device 10 is inserted and tube 42 is inverted to allow dispensing of the antigen, but not of the particulate matter that is filtered.

Figure 3:
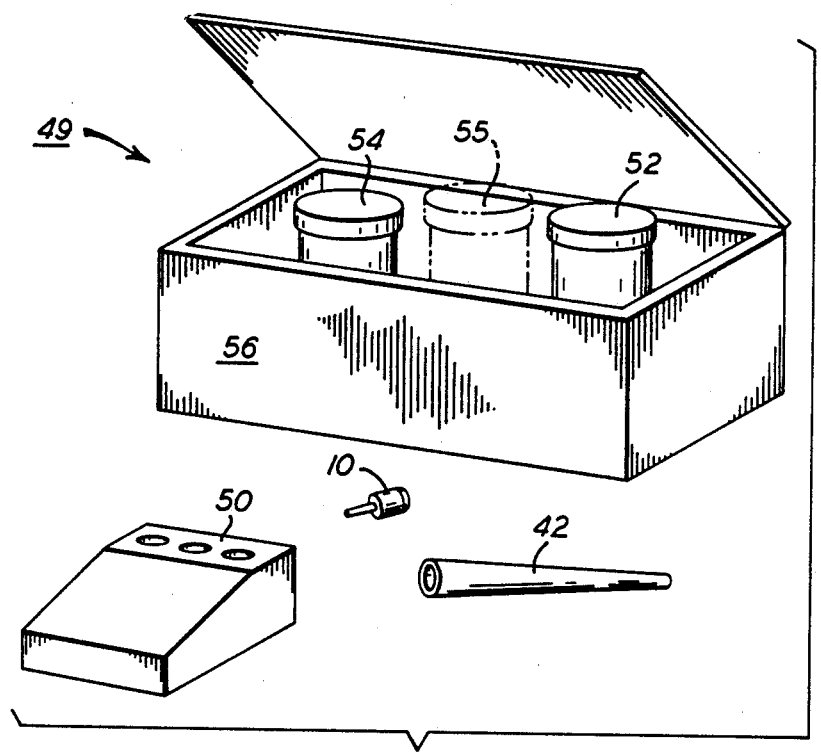
FIG. 3 is a fragmentary perspective view of a kit constructed in accordance with the invention.

Most preferably, filter device 10 of the invention is packaged in a kit form, such as kit 49, FIG. 3. Such a kit comprises filter device 10, tube 42, one or more immunoassay devices 50, a container 52 of labeled antibody used with device 50 in a conventional manner, and optionally a second container 54 that provides one or more extraction reagents to be used in tube 42. Still further, an additional optional component is a container 55, shown in phantom, of beads bearing antibodies for complexing with the target antigen, such beads being incapable of passing through the filter of assay device 50. Conveniently, all of this is packaged as in a container or box 56.

Figure 4:
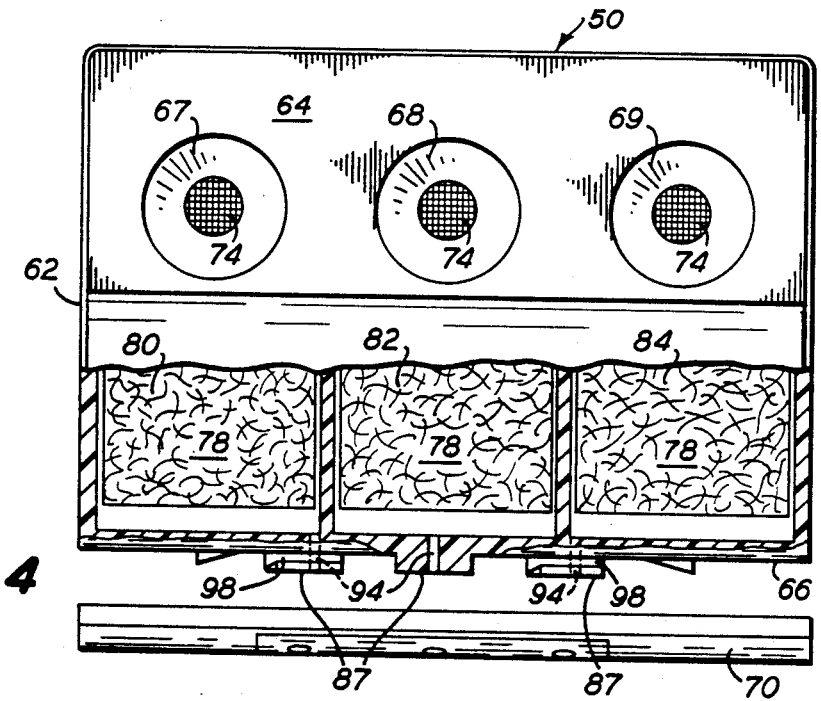
FIG. 4 is an exploded plan view, partially in section, of an immunoassay device that is part of the kit of FIG. 3.

Some details of assay device 50 are shown in FIG. 4. As is described and claim in the aforesaid U.S. Ser. No. 240,179, such a device comprise a frame 62 having a top surface 64, and a front edge 66. Mounted on edge 66 is a slide valve 70. Top surface 64 has three wells or upper compartments 67, 68 and 69. At the bottom of each of the compartments is a filter 74 of the pore sizes noted above. Filters 74 have an upper surface and an under surface, not shown, in liquid-flow contact with an absorbent material 78 that preferably occupies each of three lower compartments 80, 82 and 84, paired with the upper ones. As used herein, "liquid-flow contact" means, in sufficient proximity such that a liquid meniscus emanating from the under surface will also wet material 78 and flow into it, if no air lock exists in the lower compartment. Material 78 is any bibulous material, having a sufficient pore volume to soak up about 2 cc of liquid. Useful materials include cellulose acetate, cotton, and rayon. Useful materials for filters 74 include polyamides, such as nylons, and for example nylon-66 microporous membranes manufactured under the tradenames BIODYNE A or ULTRIPOR N-66 by Pall Corporation. Most preferably, the membranes are precoated (prior to use) with one or more water-soluble proteins, such as casein derivatives obtained from acylation, alkylation or sulfonylation of the casein.

Optionally the device can contain (between the filter and the absorbent material) a porous member which restricts flow back up to the filter, but allows flow from the filter to the absorbent material.

Vent aperture 94 is provided in each compartment 80, 82 and 84, to allow air passage out of the compartment as liquid flows in. Without such vents, or when the vent apertures are closed, an air lock precludes liquid from flowing through filter 74 into the lower compartments. Valve 70 comprises a vent bar that blocks or unblocks apertures 94 together as the bar slides to the left or right, on an interlocking track, not shown. The blocking material is a valve seat comprising an elastomeric material (not shown) that presses against the exterior surface 87 of studs 98 associated with each aperture. The elastomeric material is especially selected for durometer hardness, cold flow, and coefficient of friction that will ensure that, when the valve seats are to be slid to the side of studs 98, having been compressed by the studs an amount of about 0.15 mm, they can be slid with a force that is between about 0.15 newtons and about 20 newtons. (Anything less than about 0.15 newtons will cause member 52 to slide uncontrollably under its own weight. A force in excess of 20 newtons has been found to be too high for easy manual manipulation.)

The above list of properties is not intended to imply that the valve seats are only to be compressed 0.15 mm when bar 70 is mounted on studs 98. Instead, the compression can be from about 0 to as much as 0.3 mm. Practically speaking, however, some compression is preferred to ensure that the surface of the valve seats is in fact sealed over apertures 94. For the measurement of the force required to slide the valve, 0.15 mm compression is preferred.

To achieve the sliding force of from 0.15 to about 20 newtons, the noted properties for the elastomeric material are preferably within the following ranges: Durometer (a measure of hardness) of no greater than about 70 Shore A, and most preferably form 55 to 65 Shore A. Cold flow (a measure of loss of recovery after being deformed, also known as "compression set") of between about 10 and about 40% lost recovery when compressed at 25° C., and most preferably, 23% lost recovery. Coefficient of friction (static) against polystyrene (the preferred material for stud 98) of between about 0.3 and about 0.6, and most preferably about 0.35.

Useful materials falling within these ranges include thermoplastic rubber available under the tradename Santoprene Neutral 201-55 and 201-64, from Monsanto Corp. These two rubbers have the following specific properties:

|  | Neutral | |
| --- | --- | --- |
|  | 201-55 | 201-64 |
| Hardness | 55 Shore A | 64 Shore A |
| Spec. Gravity | 0.97 | 0.97 |
| Tensile Strength | 47 Kg/cm$^2$ | 70 Kg/cm$^2$ |
| Ultimate Elongation | 330% | 400% |
| 100% Modulus | 21 Kg/cm$^2$ | 25 Kg/cm$^2$ |
| Tear Strength (25° C.) | 19 kN/m | 24.5 kN/m |
| Tension Set | 6% | 10% |
| Cold Flow at 25° C. | 23% | 23% |
| Flex Fatigue (cycles to fail) | >3.4 million | >3.4 million |
| Brittle Point | Not Available | <60° C. |
| Static Coefficient of Friction (against polystyrene) | 0.59 | 0.35 |

Figure 5:
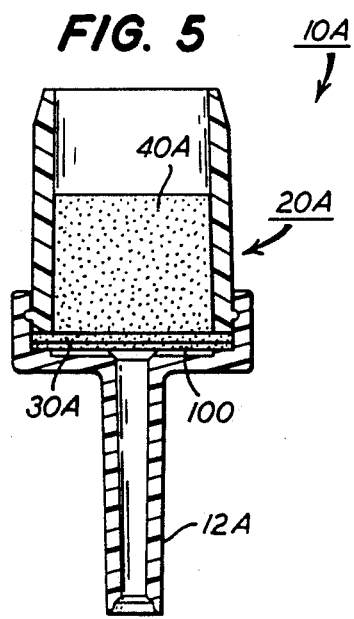
FIG. 5 is a section view similar to FIG. 1 but illustrating an alternate embodiment.

A third filter material, with a pore size intermediate that of the other two materials, can also be used, as shown in FIG. 5. Parts similar to those previously described bear the same reference numeral, to which the distinguishing suffix "A" has been appended.

Thus, filter device 10A comprises two snap-together portions 12A and 20A as before, shaped substantially the same as in the other embodiment, with the same functions. The coarser filter 40A is present as before. However, two filter membranes of a finer size are present—membrane 30A and a second membrane 100. For example, if membrane 30A has a pore size of 10 microns, then membrane 100 has a size of 5 microns. In such a case, membrane 100 is preferably the same material as used for membrane 30A, except with a smaller pore size. Or alternatively, in such a combination membrane 30A can provide a pore size of, e.g., 20 to 40 microns.

The invention has been described in detail with particular reference to preferred embodiments thereof, but it will be understood that variations and modifications can be effected within the spirit and scope of the invention.

What is claimed is:

1. In a kit for extracting and testing an antigen from body fluids, the kit including an extraction tube to which a body fluid and an extracting reagent are added to produce a solution of extracted antigen, a filter tip for insertion into said tube after adding body fluids and the extracting agent, said tip being constructed to mate with said tube;

a test device having plural test wells, filter means in each well for passing the solution through and for attaching the extracted antigen, said filter means having a predetermined average pore size, and an absorbent material underneath said filter means to draw liquid through said filter means and into said absorbent material, said test device being physically separate from said extraction tube;

and a container of labeled antibody for said antigen;

the improvement wherein said filter tip includes at least two filter media having two different predetermined pore sizes, one being a fine size and the other being a coarse size, said filter medium with said fine size being substantially the same pore size as said pore size of said test device filter means.

2. A kit as defined in claim 1, wherein said same pore size in about 5 microns.

3. A kit as defined in claim 1, wherein said other filter is selected from polyester fibers or porous polyethylene.

4. A kit as defined in claims 1 or 2, and further including in said tip a third filter having pores sized to trap particles of sizes different from those trapped by said two filters.

5. A kit as defined in claim 1, wherein either or both of said at least two filter media is coated with a surfactant.

* * * * *